United States Patent [19]

Scully et al.

[11] Patent Number: 4,600,879
[45] Date of Patent: Jul. 15, 1986

[54] WATER MOISTURE MEASURING INSTRUMENT AND METHOD

[76] Inventors: John P. Scully, 3071 Wakefield Dr., Carpentersville, Ill. 60110; Richard Ward, 1931 Prairie Sq., Schaumburg, Ill. 60195

[21] Appl. No.: 620,848

[22] Filed: Jun. 15, 1984

[51] Int. Cl.⁴ .......................................... G01R 27/04
[52] U.S. Cl. ............................................. 324/58.5 A
[58] Field of Search ........... 324/58.5 A, 58 A, 58.5 C

[56] References Cited

U.S. PATENT DOCUMENTS

| | | | |
|---|---|---|---|
| 4,103,224 | 7/1978 | Taro et al. | 324/58.5 C |
| 4,131,845 | 12/1978 | Pakulis | 324/58.5 A |
| 4,399,403 | 8/1983 | Strandberg, Jr. et al. | 324/58.5 A |
| 4,482,634 | 11/1984 | Davis, Jr. et al. | 324/58.5 A X |
| 4,484,133 | 11/1984 | Riggin | 324/58.5 A |
| 4,485,284 | 11/1984 | Pakulis | 324/58.5 A X |
| 4,486,714 | 12/1984 | Davis, Jr. et al. | 324/58.5 A X |
| 4,492,915 | 1/1985 | Caspers | 324/58.5 A X |
| 4,499,418 | 2/1985 | Helms et al. | 324/58.5 A |

FOREIGN PATENT DOCUMENTS

| | | | |
|---|---|---|---|
| 1068166 | 5/1967 | United Kingdom | 324/58.5 A |
| 0253186 | 11/1970 | U.S.S.R. | 324/58.5 A |

OTHER PUBLICATIONS

Kulinski et al, Microwave On-Line Moisture Content Monitoring in Low-Hydrated Organic Materials, Proceedings of the 10th European Microwave Conference, Warsaw, Poland, Sep. 8-12, 1980, pp. 221-226.

Primary Examiner—Stanley T. Krawczewicz
Attorney, Agent, or Firm—Aaron Passman

[57] ABSTRACT

Shown is an apparatus and method of use where microwaves transmitted through volatiles include water vapor driven from an adequate polymer sample by heating in a closed test cell. A pump moves a predried gas and those volatiles at pressure and flow rate to a microwave transducer including a pair of antennae horns aimed at one another, one with a microwave transmitter oscillator and the other with a receiver detector. The volatiles are brought transversely across the open end of the oscillator antenna horn by a conduit. The particular orientation of the conduit is important to the accuracy of the measurement. A moisture absorbent material inserted axially into the conduit restrains the flow of volatiles changing same to liquid form. Loss of microwave energy due to the water vapors in the volatiles is measured at the output of the detector. Microwave energy absorbent material surrounds the transducer.

11 Claims, 5 Drawing Figures

WATER MOISTURE MEASURING INSTRUMENT AND METHOD

BACKGROUND OF THE DISCLOSURE

This disclosure relates to water moisture measuring instruments using microwave transducers and more particularly those instruments which measure the water moisture in plastic pellets as used to make molded parts.

Microwaves are not the only way of checking water moisture and polymer pellets are not the only material which must be examined. In the paper manufacturing and laminated wood business, the use of reflected infrared energy has been applied to measure water moisture in an on line production operation. That approach is adequate for water moisture measurements of the surface water but does not give detailed and accurate information concerning water moisture within the product. The Anacon, Inc., Optical Moisture Measurement Apparatus made in Massachusetts is one example of that type of surface water moisture measuring apparatus.

There are other approaches which use dielectric measuring devices which monitor the ability of the water in the moist substance being transduced to pass electric current. The greater the level of water moisture the more current will pass, consequently some measurement of water moisture content is ascertainable. These devices are accurate only when the water moisture levels are as high as 25 to 30 percent and the accuracy with which the measurement must be made relatively low. Dielectric devices are made by Axiomatics Corp. of Sudbury, Mass.; Gann of Stuttgart, Germany and others.

Microwaves have been used to measure water moisture at relatively high levels in products such as grain and cereal. In such applications those products were in a chute across which a microwave beam was passed between a transmitter and its receiver. Water moisture readings were taken at high speeds or on batches moving or retained in for example an entry chute for a processor, dryer or the like. With such an arrangement water moisture levels of ten to fifty percent were measurable with a tolerance of plus or minus a few percent or more. Generally those microwave devices employ the frequencies of C and X microwave radiation bands. Devices of that type are made by Advanced Moisture Technology Inc of Waconda, Ill. (under the brand name of Aqua Trace); Omega Controls of Santa Ana, Calif. and others make and sell similar equipment. The problem with those devices is their inability to measure the extremely low levels of water moisture present in polymeric substances such as molding pellets and more specifically, to accurately measure between one low water moisture level and another.

It has been recognized that other scientific principles and approaches could also be beneficially adopted for application in measuring the low levels of water moisture in polymeric pellets. The DuPont Company of Wilmington, Del. has developed and sold a series of instruments which use the principal of electrolysis to measure the amount of water present in a gas sample of the volatiles from a very few polymer pellets. In particular a dry nitrogen gas sample is used to transfer the water vapor and volatiles rising off of a very small heated sample of the polymer pellets usually less than a gram, i.e., a dozen pellets. The volatiles are plasticizers, mold release materials, antioxidants and other similar non aqueous volatiles. Those water vapors and volatiles are then passed to an electrolytic cell having a phosphorus pentoxide film positioned between two electrodes. The phosphorus pentoxide film absorbs the water vapor which can then be electrolyzed by current passing between the electrodes. The electrode current changes the water to hydrogen and oxygen which is passed by dry nitrogen gas to coulometrically regenerate the phosphorus pentoxide. The amount of current required corresponds to the amount of water which was present in the polymer sample. The problems with this approach are that only a very small sample can be tested usually a gram or less in weight, volatiles tend to plug or foul the electrolytic cell and the test procedure is a very sophisticated laboratory procedure. Consequently, the use of the DuPont apparatus is time consuming and its accuracy has been found suspect due to the small sample and ease with which slight operational and procedural errors can dramatically influence the results.

Mitsubishi Chemical Industries, Ltd. of Japan and others make water moisture meters which uses the principal of the Karl Fischer reagent reaction to measure water moisture. This is a titration performed on a sample of the water vapor and volatiles obtained by heating a sample and carrying same by means of a dry gas to the titration cell. The amount of water vapor present is directly related to the reaction which is a function of the purity and concentration of titration solution. The problem with this arrangement is that it also requires skilled scientists to operate the instrument and insure that the chemicals used are and remain of the proper concentration and quality. The volatiles in the sample used with this procedure can cause false readings. The DuPont and Mitsubishi instruments are strictly laboratory devices and are not practical for use in a plant environment where adequate sample size must be tested quickly and accurately to determine even small changes in percent water moisture. While laboratory uses for water moisture data exist, the commercial need is infinitely greater.

A variety of patents have been issued which show particular constructions for microwave water moisture measuring apparatus; the teaching of those patents are incorporated herein and made a part hereof by reference. Such patents include specific structural configurations which have been found to work well in connection with measurement of water moisture in bulk materials. The Pakulis patent to U.S. Pat. No. 4,131,845 has a chute construction for receiving water moisture containing material. The chute is generally rectangular and has the microwave transmitter and detector mounted across from one another on opposite sides of the chute. Microwaves are used to detect water moisture and gamma rays are used to detect density and with that information the percent water moisture can be calculated. To this approach is added a microwave absorber material. In particular, Eccosorb foam sold by Emerson and Cummings, Inc., is provided to internally line the chute. Rectangular and cylindrical chutes are shown in plan views and the shape of the chute is non tapering having straight sidewalls.

In contrast the Walker patent U.S. Pat. No. 3,818,333 shows a frusto conical chute with a funnel-like structure which has microwave detectors and transmitters positioned at the lower narrow end of the chute. A window is included in front of the oscillator to prevent the microwaves from being transmitted as a surface wave across the inner surface of the chute. Therefore it is understood that the positioning of the microwave transmitter and detector in a particular chute construction may have some influence on the accuracy of the microwave water moisture measurements. In particular, when the microwave beam is directly perpendicular to the products moving through the chute and therefore (between the microwave transmitter and receiver antenna or horns) microwaves reflected between the horns cause standing wave patterns resulting in the inaccuracies. Specifically, it is believed that a portion of the microwaves passing through the product will be scattered so as to miss the receiving horn likewise resulting in inaccurate measurements. When the product is confined in a chute additional inaccuracies arise from microwaves traveling axially along the chute. Therefore, recognition of the importance of the positioning of the test sample relative to the microwave beam and the isolation of the test container by means of absorbent material have to a limited degree been considered, but not sufficiently to provide the accuracy level necessary for measurement of slight variations in water moisture level.

The phenomenon of loss of microwave energy due to the presence of water vapor is set forth in the U.S. Pat. No. 4,103,224 to Taro, et al. Moreover, the influence of air pressure and temperature on the water vapor measurement is therein considered and discussed. Specifically, the humidity of air and/or any gas can be determined by measuring the value Q of the resonator for microwave energy, i.e., the loss of microwave energy. The Taro, et al, structure has the transmitter in the middle of the chamber defined by the housing and the receiver(s) are carried by the walls of the housing. Therefore the water moisture in the gas surrounding the transmitter is being measured by detection of microwave energy loss. That construction is different from the conventional teachings of Breazeale U.S. Pat. No. 2,659,860 and Brunton et al, U.S. Pat. No. 3,460,030 which illustrate an approach wherein the transmitter is positioned across from the receiver detector and therebetween is the sample of process material. All the patents appreciate the importance of positioning the antennae horns for transmitter and detector relative to the sample to be tested, but use varying approaches. Similarly, circuitry for application and measurement of microwaves is detailed in each patent. Updating of the circuitry with respect to solid state and microprocessor technology is discussed in the U.S. Pat. to Wiles No. 3,815,019 which includes a Gunn diode for transmitting a signal having a frequency between 20 and 25 GHz and that transmitted signal is picked up by a thermistor detector.

It has therefore been an unsolved problem to develop a specific instrument, for water moisture measurement of plastic molding pellets, which is sensitive to low levels of water moisture and small variations of water moisture content. Moreover it has been difficult to provide a reliable transducer for a sample large enough to be representative of a normal quantity of polymeric pellets as used in the manufacture of typical molded plastic components. It is particularly important that the water moisture level of such plastic pellets be accurately known in order that they can be adequately pre-dried prior to molding. The vast energy requirements for pre-drying operations is extremely costly particularly in connection with the processing of high volumes of plastic pellets as used in the manufacture of large and expensive molded components. When too much water moisture is present, the parts are difficult to mold correctly as the water moisture becomes steam and interferes with the molding process. Consequently, the poorly produced parts have to be reground, redried and remolded thereby doubling the cost of production and lowering overall quality since reground plastic material is not as easy to mold as new material. Therefore, it is essential to be able to measure the percentage of water moisture in a representative sample before and/or after a drying operation so as to accurately determine whether the material is acceptable for use in molding.

It is an object of the present invention to teach a microwave transducer, its structural arrangement and method of use for measurement of relatively low percentages of polymeric water moisture content thereby accurately defining small variations in polymeric water moisture levels.

It is a still further object of the invention disclosed herein to show an apparatus which has a heated sample cell for separating volatiles from an adequate plastic sample whereby a dried gas at a known flow rate can be used to transfer the volatiles to a microwave beam in which the low levels of water moisture can be quickly and accurately measured by detection of microwave energy lost.

It is yet another feature of this invention to disclose a preferred embodiment which has been shown to give accurate and repeatable measurements for low levels of water moisture in pellets of polymer.

BRIEF SUMMARY OF THE DISCLOSURE

Consistent with the foregoing objects and in order to overcome the problems and difficulties of the prior instruments and methods, the disclosure herein includes an apparatus and its method for use in which microwaves are transmitted through volatiles from an adequate polymer sample to thereby provide an accurate water moisture measurement. Disclosed is a test instrument for use in measuring low levels of water moisture in polymeric materials and it includes a heated test cell in which an adequate sample of about 80 grams of plastic pellets are therein heated to drive off the volatiles. Those volatiles include water vapor which by means of a pump supplying a predried gas at a pre-established pressure level and a known flow rate, are transferred to a specifically designed microwave transducer test cell.

The conduit for transferring the dried gas and carrying the volatiles is transparent to microwave radiation and the conduit is specifically aligned across the microwave beam transverse to the transducer test cell to maximize the access of the beam to the water moisture and the volatiles restrained by a moisture absorber. The cell has a cylinder shape with the antennae horns located at the open ends of the cylinder. The horns are positioned so that their elongated rectangular open mouths cover the cylindrical circular open ends of a relatively short length of small diameter plastic pipe that forms the cell housing. The antennae horns are across from but aligned with respect to one another and the plastic pipe is externally surrounded with a microwave absorbent material, such as Eccosorb foam. The conduit passes transversely through the plastic pipe in close axial proximity to the open end of the oscillator transmitter antenna horn such that it is transversely across the longer sides of the rectangular opening of the oscillator transmitter antenna horn. In particular, the conduit is transverse across the middle of the longer sides of the rectangularly shaped microwave antenna horn for the oscillator transmitter and is positioned especially and particularly proximate to the rectangular opening for the antenna horn for the oscillator transmitter. It has been found that this transverse centered position close to the oscillator transmitter provides accuracy and measurement repeatability for the transducer test cell.

The transducer test cell includes a Gunn oscillator as the microwave transmitter mounted to its antenna horn and aligned with and across from the microwave receiver detector. The loss of microwave energy transmission between the transmitter and detector is a measure of the amount of water moisture from the gas sample. More specifically, a constant voltage power supply is used for the Gunn oscillator and the output of the receiver detector is less than the microwave energy transmitted and varies as a consequence of the water moisture from the test sample. The transducer test cell is surrounded by a microwave absorber, such as Eccosorb foam, to prevent scattered or reflected microwave energy from being detected by the receiver. That is to say that, some of the microwaves being transmitted react with the water moisture in the sample gas, others are scattered and absorbed by the Eccosorb foam and the remaining microwaves are thereafter detected. Therefore, the scattered and reflected microwaves are not available for measurement by the detector. Accurate measurement requires that only those microwaves which are transmitted and passed through the vapor/volatile gas sample (and are not absorbed by the foam or water present) are detected. There is no other possibility for the transmitted microwaves to reach the detector receiver without having been available to the vapor/volatile.

The microwave reaction with the water vapor is based upon absorption of the microwave energy by the water molecule. While not entirely known or understood, the moisture absorber restrains the water from the gas sample and volatiles in the molecular form which can be measured by microwave absorption. It can't be measured in the polymer sample because the water therein is hydrogen bonded which changes the rotational energy such that it cannot absorb microwave energy. Surface water on the polymer represents only a small portion of the total moisture.

It has been explained that the conduit has to be specifically positioned between the transmitter and detector in order to get accurate and repeatable readings. In addition, a moisture absorbing material must be axially inserted up the conduit in order to assure resident time of the volatile/vapor gas sample sufficient to allow absorption of the moisture and location of same within the microwave beam to accurately monitor water moisture measurement. The specific axial position (into the conduit) of the moisture absorber relative to the beam of microwave energy is kept constant so as to avoid the introduction of another variable for the instrument to measure. Once the axial insertion point has been determined, it need not be revised. This instrument can therefore be synchronized mechanically with respect to other similar instruments merely by particular placement of the moisture absorbing material.

DETAILED DESCRIPTION OF THE DRAWINGS

Figure 1:
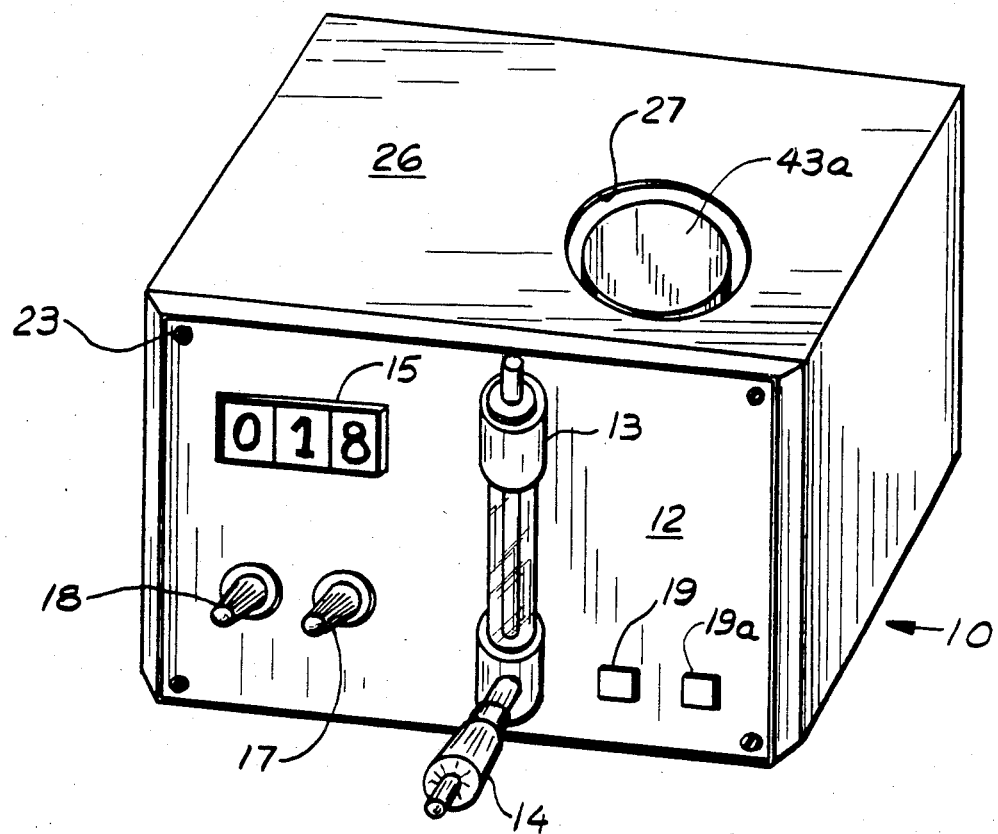
FIG. 1 is a perspective view outside of the housing and in particular the control panel for the microwave measuring instrument of the present disclosure.

FIG. 1 shows instrument 10 for measuring water moisture in a polymer sample by means of microwave energy and includes a generally cube like housing 11 with a front panel 12 which supports the controls and readout meter for the instrument 10. In particular there is a Gilmont Instruments, Inc. flow meter 13 which in the preferred embodiment is mounted to the front panel 12 and connected with its inlets and outlets passing therethrough, see FIG. 2 for details. The flow meter 13 has a micrometer adjustment 14 which is used to set the flow rate at a preferred level. In this particular instance, the flow rate is 30 milliliters per minute. The material flowing is a dried air or gas which is used to convey the volatiles to a microwave transducer test cell as will be explained. Adjacent the flow meter 13 there is a digital readout 15 meter which is used to display the amount of water moisture in the sample. Since the sample is preweighed and the density is known the reading on the meter 15 gives the percent water moisture level with respect to the test sample since all samples of the same material have the same weight, about 80 grams. Beneath the meter 15 there are two control knobs, one knob designated 17 is for zeroing the instrument prior to use at the beginning of the test. The other knob, 18 is to establish the level of sensitivity of the instrument during the test. The front panel 12 has a start button 19 which is used to begin the test and a reset button 19a which is used to reset the test timer after a test has been completed.

Figure 2:
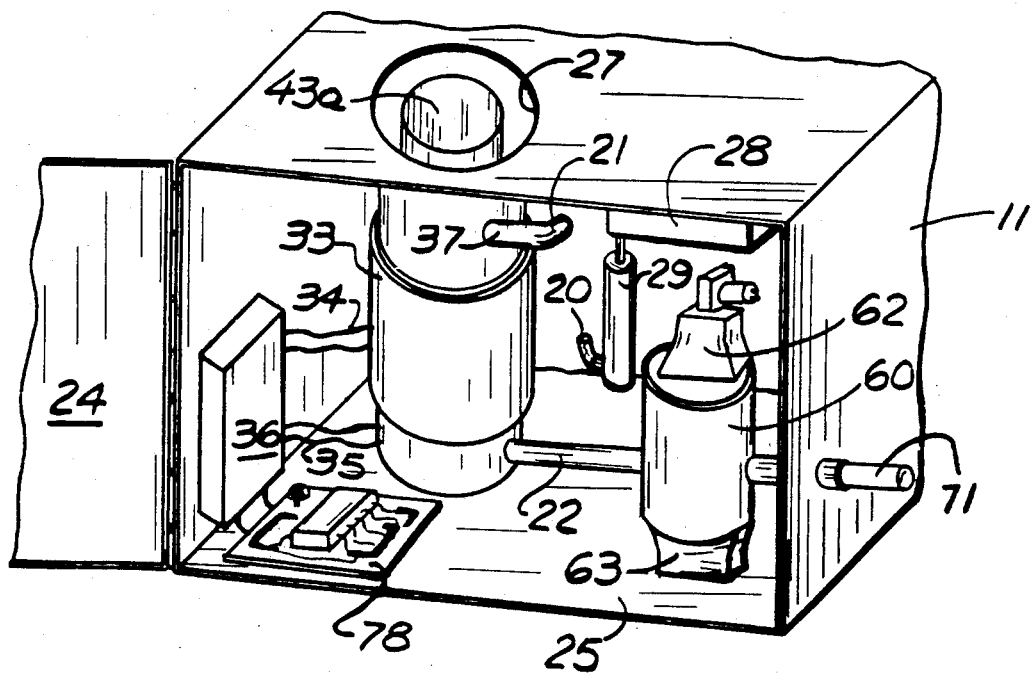
FIG. 2 is an elevational view of the open back of the instrument of FIG. 1 showing the location of the key components.

Turning now to FIG. 2 wherein the basic components of instrument 10 are shown through the open back of the housing 11 there is the inlet 20 from the bottom of flow meter 13 and the outlet 21 from the top of flow meter. Outlet 21 is connected to a Teflon tube 22 which has a ⅜ inch diameter and is used throughout the instrument to transport gases that are measured by microwave energy. Teflon tubing is transparent to microwave energy. The front panel 12 is affixed to housing 11 by means of screws 23. While not critical to the housing 11 there are the various sides which are provided for the safety of the user and act as structural components. There is the bottom 25, the back panel 24 and the top panel 26. These components are used to support the structures which make up the instrument 10. The top 26 contains a circular hole 27 for an operator to reach down and to open up the heating cell whereby pellets of polymer material may be placed in the heating cell to test.

In FIG. 2 there is shown a small air pump 28 which is of the type used to supply air to an aquarium. It has an electromagnetic motor which vibrates a bellows or diaphragm to pump air. Air pump 28 supplies ambient air to a dryer 29 such as a Gas-Dry Filter Trap made by Chemical Research Supplies, Inc., of Illinois. This dryer 29 has a hollow acrylic tube which permits visual observation of the condition of the Drierite desiccant which changes from blue to red over its entire length when the material is saturated. The air from pump 28 enters at the top of the dryer 29 then passes therethrough to an exit at the bottom where it is connected to inlet 20 for the flow meter 13. The air which has been predried then passes through the flow meter 13 exiting at the outlet 21 wherefrom it passes into the heating test cell 30. Tubing 22 is used throughout the instrument to make the connections and transmit the dried regulated air from one portion of the instrument 10 to another.

Figure 3:
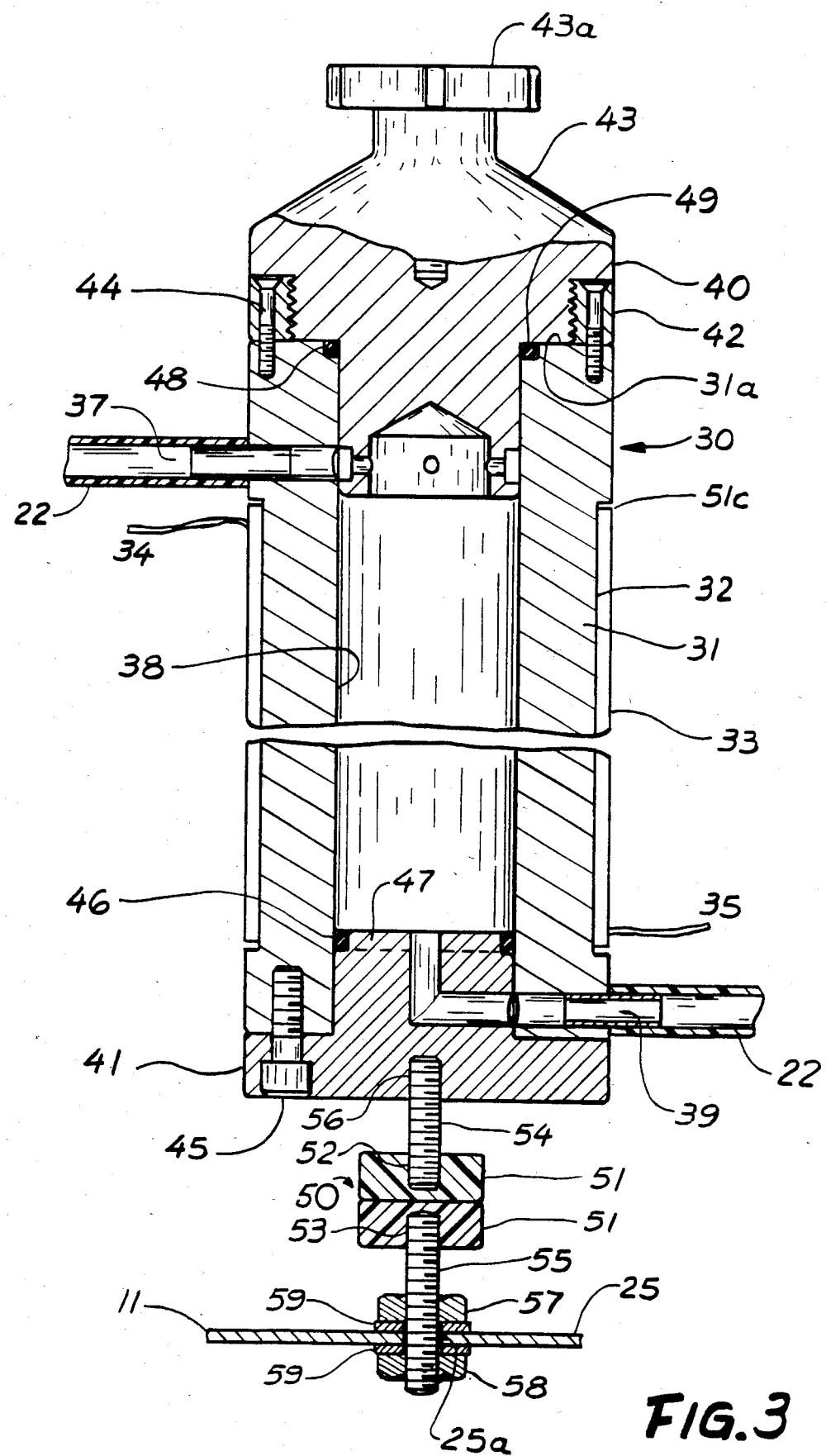
FIG. 3 is a side view in cross-section of the heating test cell which is used to drive the volatiles from a polymer test sample for use thereafter in microwave water moisture measurement.

Turning now to FIG. 3 wherein the details of the heating test cell 30 are shown in a cross sectional view. In particular, there is a cylindrical shaped body 31 which is the main physical and structural element of the heating cell 30, body 31 is a hollow metal tube with a surface recess 32 about its outer periphery. Recess 32 is adapted to support a heating jacket 33 such as for example the Ogden Manufacturing Co. of Arlington Heights, Ill. heater model number B27 SL 70A7 which is a 600 watt, 120 volt heater having a seven inch length and a $2\frac{3}{4}$ inch diameter designed to circumscribe tightly the recess 32 on the body 31. This heater jacket 33 has electrical connections 34 and 35 which are connected to a controller thermostat 36 shown best in FIG. 2. The controller thermostat 36 is also supplied by Ogden Manufacturing Co. of Arlington Heights, Ill. and is model ETR3 which is capable of accurately controlling the temperature to the required degree. Controller thermostat 36 has an adjustment knob which may be set for the specific temperature required within the heating cell 30. In FIGS. 2 and 3 the upper inlet 37 for the heating cell 30 is connected to tubing 22 from the flow meter 13 outlet 21 and passes the flow regulated dry air into an internal chamber 38 of the heating cell 30. The air is then transmitted longitudinally downward through the chamber 38 to an exit outlet 39 at the bottom of the chamber. The chamber 38 is designed to contain and heat polymer pellets thereby driving volatiles therefrom so that the volatiles can be carried by the dry air. More specifically and with regard to the construction, the body 31 being a hollow aluminum tube has an upper end closure 40 and a lower end closure 41. Lower end closure 41 is a cylindrical plate through which a hole has been provided to permit exit passage 39 to extend therethrough and connect to tubing 22. Similarly upper end closure 40 consists of two pieces; a nut 42 is mounted to the upper end of the body 31 to provide a threaded opening for chamber 38 and to receive a cap 43 which has a set of male threads to be received by nut 42. Nut 42 is retained on the body 31 by retaining screws 44 only two of which is shown in FIG. 3. Similarly the lower end closure 41 is held to the body 31 by means of filister head screws 45 (only one of which is shown). In order to seal the lower end closure 41 to the body there is an O-ring 46 which fits around a recessed upper shoulder 47 on the lower end closure 41 and engages the inside wall of the sample chamber 38 to form a tightly sealed bottom closure. Attached to cap 43 is the insulating knob 43a whereby rotary movement of knob 43a will unscrew cap 43 from the nut 42 and leave open the upper end of the heating cell 30 chamber 38. To seal tightly the cap 43 against the body 31, there is a recessed groove 48 cut in the upper end face 31a of the body 31 which groove 48 supports an O-ring 49 in position to contact the lower side of the cap 43.

To mount the heating cell 30 to the housing 11 and more particularly to the bottom 25 thereof and yet protect the same from heat there is an insulated mounting structure 50, see FIG. 3. Mounting structure 50 consists of an insulator 51 and a pair of threaded openings 52 and 53 in opposite ends of the insulator 51. These openings are adapted to receive support studs upper 54 and lower 55 which extend outwardly therefrom to the lower end closure 41 and the housing bottom 25 respectively. In particular the lower end closure 41 has a centrally disposed threaded opening 56 which receives the upper stud 54 for threaded engagement. Similarly, the housing bottom 25 has a hole 25a and by means of a pair of jam nuts 57 and 58 with cooperating washers 59 the lower stud 55 is secured upright to the bottom 25 of housing 11.

Figure 4:
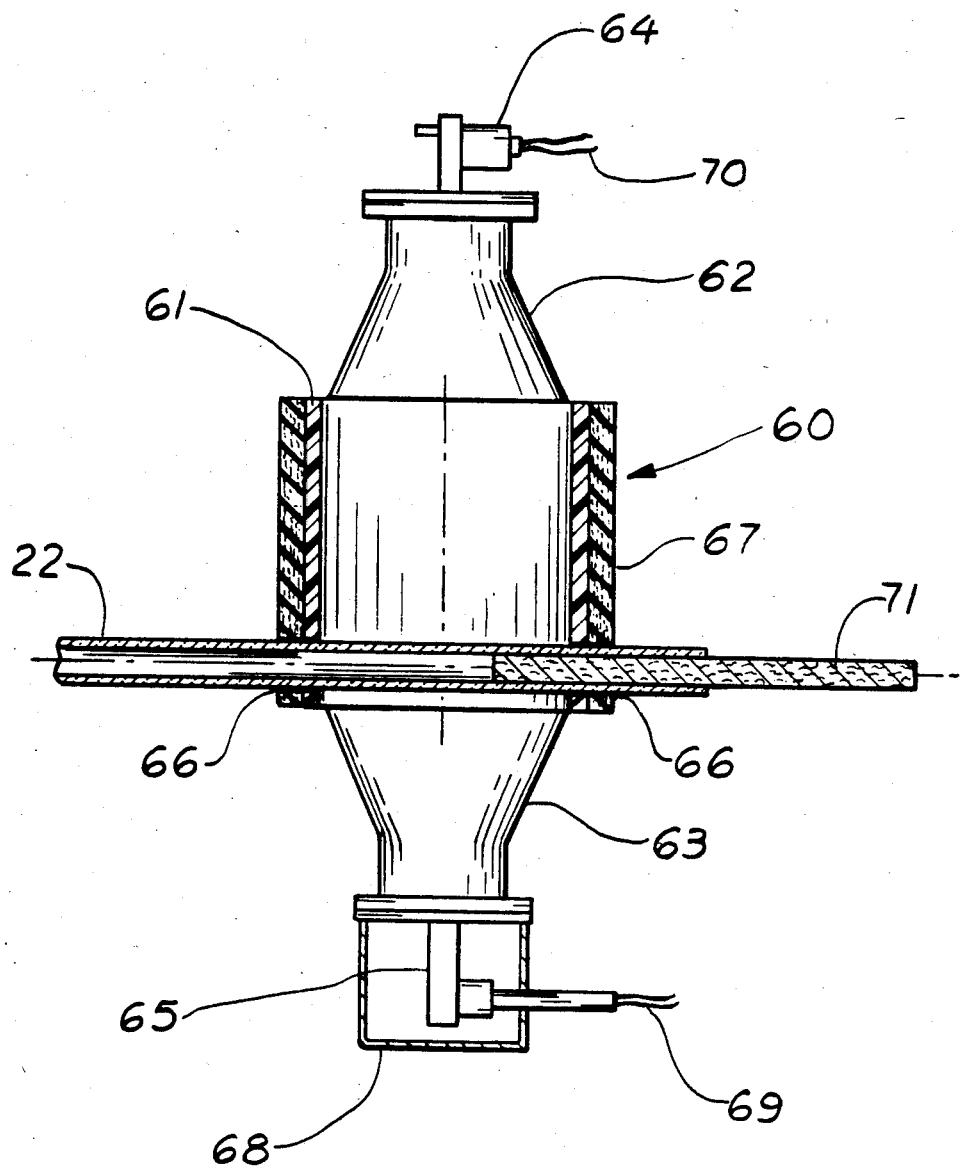
FIG. 4 is a side view in cross-section of the microwave transducer test cell wherein a microwave beam between an oscillator and detector are used to measure microwave energy loss due to water vapor in the volatiles from the test sample.

It will no doubt be appreciated that the polymer sample, about 80 grams of pellets, can be placed within the sample chamber 38 of the heating cell 30 by means of removing the cap 43. Once the polymer pellets are placed therein, sealed with the cap 43 and heated by means of heating jacket 33 which is controlled by thermostat 36 the volatiles including water vapor are driven from the pellets in the chamber 38. The predried gas at a preset flow rate enters at inlet passage 37 and passes through the heated polymer sample before exiting at passage 39 to be conveyed by a further extension of tubing 22 to the transducer test cell 60 as best shown in FIGS. 2 and 4. The transducer test cell 60 is generally cylindrical and hollow and in particular includes a main support tube 61 which is PVC polymeric tubing having an outside diameter of about $2\frac{3}{8}$ inches and an inside diameter of just under 2 inches. Tubing 61 is about two inches long and is used to support in opposed aligned relation a pair of rectangularly frusto-conical antennae horns such as those made by M/A-Com Gallium Arsenide Products, Inc. of Burlington, Mass., being their model number MA86552. In particular, there is an oscillator horn 62 and a detector horn 63; each being identical and parallel but facing one another with their open ends in opposed aligned parallel relation across the ends of ends of tubing 61. The open ends of the horns are secured by adhesive applied to at their contact with tube 61. The narrower or closed end of the horn is adapted to mount and support a detector 64 or an oscillator 65, see FIG. 4. Specifically the oscillator 65 is a K Band commercial Gunn Oscillator Model MA86790 as made by the M/A-Com Gallium Arsenide Products, Inc of Burlington, Mass. and it puts out a signal in the range of 24 GHz. This type of oscillator 65 is normally used in connection with Doppler Radar Systems, Police Speed Radar, Microwave Beam Interrupt Counters, Traffic Control and Microwave Barriers (perimeter protection). These oscillators 65 are not used normally in connection with water moisture measurement. Similarly, and manufactured and distributed by a division of the same company, called Microwave Associates, Inc. also of Burlington, Mass., the K-Band Microwave Sensor, Model MA-86561 is used as the detector in this instrument 10 and in particular the sensor consists of a wave guide holder and Schottky Detector Diode designed for commercial use at about 24 GHz with audio frequency IF's. Consequently, the oscillator 65 and the detector 64 are approximately six inches apart from one another when mounted to their respective oscillator horns 62 and detector horns 63 as attached to the tubing 61.

Through the tube 61 there is a transverse hole 66 which provides an opening to receive the further extension of tube 22 that carries the volatiles and gases. The position of the hole 66 is transverse to the longer dimension of the aligned antennae horns. Moreover, it is axially close to the antenna horn 63 for the oscillator 65. In particular, the open ends of the antennae horns 62 and 63 at the tubing 61 has an elongated dimension of 1.81 inches and the shorter dimension is 1.4 inches. The location of the further tube 22 is transverse to the 1.81 inch dimension.

Surrounding the outside of tube 61 is a microwave absorber material 67 which is Eccosorb foam type LS-30 about ¼ inch thick made by Emerson & Cummings, Inc., Gardena, Calif. This material is a foam and it is designed to absorb scattered and reflected microwaves whereby microwaves passing from the oscillator 65 through its horn 63 will pass through transverse tubing 22 which is made of Teflon polymer and is transparent to microwave energy. Antenna horn 62 and its detector 64 receive the microwave energy not absorbed by material 67 or water vapor in the gas sample. The response of oscillator 65 tends to drift due to changes in ambient temperature thereabouts during the operation of the instrument 10. Therefore a heater in the form of a U-shaped resistant element 68 has been added about the environs of the oscillator 65 in order to elevate the ambient temperature of the surroundings of the oscillator 65 and thereby stabilize its operation. This is particularly important in connection with an instrument of this type because of its sensitivity and ability to measure small changes in water moisture content. In operation, the oscillator 65 is supplied with power such as five volts DC current to energize oscillator 65; this power is supplied through line 69. The detector 64 has its connection 70 which goes to the circuit used to evaluate the amount of energy loss in the transmission between the oscillator 65 and the detector 64. Energy loss is a function of the water moisture in the volatile sample passing through the transverse tube 22 in cell 60.

In order to prevent influx of outside air and to restrain flow of the volatile and water vapor in the transverse tube 22 within the transducer cell 60 there is a water moisture absorber 71 inserted axially up into the tube 22 so as to be within the transducer cell 60. Moisture absorber 71 is a cellulose acetate fiber product with a polyester film wrap and is distributed by the Murdock Company, Inc. of Arlington Heights, Ill. as MC8627 filter element being 8.0 mm in diameter plus or minus 0.25 mm and 89.5 mm long plus or minus 0.6 mm. The average weight per unit is approximately 1.01 grams. This product is a filter element and is designed as such to be used in entirely different applications from the present instrument 10. These moisture absorbers 71 are pretreated to a uniform dryness prior to use in connection with the measurement of water moisture driven off of a polymer sample. The pretreatment consists of heating in an oven for eight hours at 120 degrees F. Instrument 10 has to be precalibrated by means of determining the distance to which to moisture absorber 71 must be axially inserted into the transverse tubing 22 in transducer cell 60. That distance is a function of the transducer cell 60 being the absorber foam 67 and microwave components, i.e., 62, 63, 64 and 65. Once this distance is found and the instrument 10 marked, all subsequent moisture absorbers will be able to be inserted to the same axial position thus providing consistency of the testing.

Figure 5:
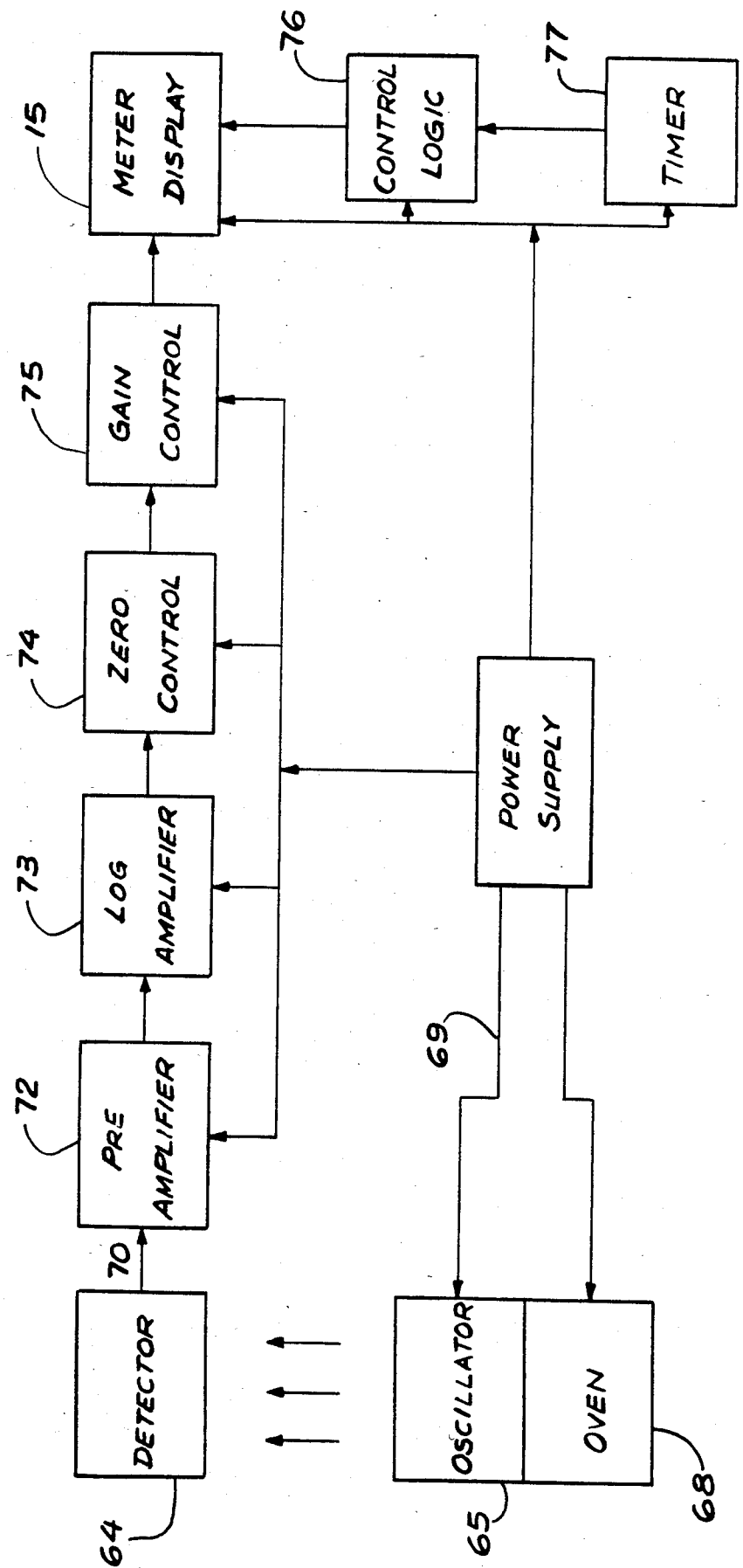
FIG. 5 is a block diagram for the circuit used for selectively comparing the difference in energy applied at the oscillator and received at the detector in the microwave transducer of the present instrument.

In FIG. 5, a block diaphragm for the circuitry is shown. The oscillator 65 and its above ambient heater element 68 are shown supplied with power through line 69. The oscillator 65 emits a signal which represents an output of the detector 64 in the form of a DC voltage proportional to the signal strength of the oscillator 65 subject only to the amount of energy lost due to water moisture in the gas sample. Without any water moisture in the gas sample, the normal loss of microwave energy in the transducer cell 60 due to the microwave absorber 67 can be measured and the readings of percent water moisture obtained. The signal from detector 64 is slight as transmitted via line 70 to a preamplifier 72 by a suitable connection which is included to increase the gain approximately ten times to an acceptable level for measurement. Since the signal is not linear it is passed from the preamplifier 72 to a log amplifier 73. The log amplifier 73 takes the preamplified signal (which is a measure of the energy absorbed due to water vapor from the volatile gas sample) and converts that signal from a log function to a linear function. The output from the log amplifier 73 is sent through a line to a zero control 74 being a calibration device to shift the signal to a zero point. Zero control 74 which is adjustably set by knob 17 on front panel 12, see FIG. 1, accounts for the drift of the electronic components and variations in the absorber density of the moisture absorber 71. Similarly, a gain control 75 which operates on the signal received from the zero control 74 to adjust the sensitivity of the instrument 10 again by means of the knob 18 on the front panel 12 of the housing 11. The output from the gain control 75 is connected to be displayed on the meter 15 which in this particular application is a digital readout.

While the instrument 10 can during the operation be allowed to continuously provide readings at meter 15, the changing in readings as a consequence of the requirement that instrument 10 reach a point when most of the water has been absorbed from the volatiles. The final reading of percent water moisture is automatically taken because it is difficult for an unskilled operator to ascertain when a proper reading should be taken. To solve that problem, there is a control logic 76 and an associated timer 77 which are used to disconnect the meter display at the start of a test and to prevent display until such time has elapsed whereby an accurate measurement of the water moisture in the gas sample can be obtained. Depending on the type of polymer material being used in the test, this time period could vary from two to fifteen minutes with most tests taking somewhere around 15 minutes. The control logic and its timer 77 are merely a start and reset arrangement, which once the instrument 10 has been loaded with the approximately 80 grams of polymer pellets and the unit has been zeroed it can be used. A start button 19 on the front panel 12 begins the time period for analyzing the volatiles driven from the test polymer. At the end of the test after the final reading has been taken a reset button 19a also on the front panel 12 can be pressed to reset the control logic 76 and timer 77 in order to begin the operation again.

The steps in operation are to set the zero to calibrate the instrument then insert and seal the sample polymer into the heating cell 30 start the timer display by pressing the start button 19 which operates the unit to drive off the volatiles from the polymer sample and transmit them to the transducer test cell 60. When the timer stops the meter first shows a fixed value which remains on the meter 15 and will not vary. In the preferred arrangement, this usually happens after a time period of about 15 minutes has elapsed. To begin the procedure again, the reset button 19a is pressed and the instrument 10 may be used once again. All of the foregoing circuitry is compactly disposed upon a printed circuit board 78, see FIG. 2.

From the foregoing it should be obvious that the construction and operation of the unit can be varied by skilled practitioners without departing from the scope of the invention as set forth in the claims which follow.

What is claimed is:

1. A water moisture measuring instrument wherein the microwave energy absorbed by the water moisture from a sample is monitored by detection of microwave energy comprising:

a source of gas having a pre-established dryness at a preset pressure and being conveyed and supplied in a conduit, a means for driving volatiles from a polymer sample connected to said conduit supply and arranged with a further conduit for thereafter transmitting said volatiles and gas from said means for driving, a microwave transducer cell being a non-metallic enclosure having a microwave oscillator and detector positioned across from and in alignment with one another and having said further conduit passing therebetween and in a predetermined position relative to the microwave beam between said oscillator and detector, a microwave absorber material surrounding said transducer cell to prevent scattered and reflected microwaves from passing to said detector, a moisture absorber adjustably positioned axially along and within said further conduit for controlling the pressure and flow of said volatiles and gas within said microwave beam, and electronic circuitry connected to said oscillator and detector to register output of said detector as a consequence of water moisture in said moisture absorber.

2. The water moisture measuring instrument of claim 1 wherein said predetermined position of said further conduit is proximate said microwave oscillator.

3. The water moisture measuring instrument of claim 2 wherein said oscillator and detector are equipped with antennae horns attached to said non-metallic enclosure which are aligned with and pointed toward one another but in spaced apart parallel relation.

4. The water moisture measuring instrument of claim 3 wherein said antennae horns are rectangular in cross section and frusto-conical in shape and said further conduit is transverse to and proximate with the open end of said oscillator antenna horn.

5. The water moisture measuring in instrument of claim 4 wherein said further conduit is transverse to the longer sides of said rectangular antenna horn of said oscillator.

6. The water moisture measuring instrument of claim 5 wherein said oscillator is kept at a pre-established operating temperature by a heater element in order to avoid operational drift.

7. The water moisture measuring instrument of claim 6 wherein said oscillator oscillates at about 24 GHz.

8. The water moisture measuring instrument of claim 7 wherein said oscillator and detector antennae horns separated by said enclosure being a hollow non-metallic of circular cross-section tube such that there is no structural path to carry microwave energy therebetween and said non-metallic tube is surrounded by a microwave absorber to prevent scattering, standing waves and reflected microwave energy from passing between said oscillator and detector.

9. The water moisture measuring instrument of claim 8 wherein said conduit and said further conduit are of a polymeric material which is substantially transparent to microwave energy.

10. The water moisture measuring instrument of claim 9 wherein said moisture absorber is a cellulose acetate fiber product with a polyester film wrap.

11. A method for determining the amount of water moisture in the volatilized gaseous sample from a sealed container having a sample of polymer molding pellets by use of microwave measuring techniques comprising the following steps;

producing volatiles from the polymer sample by heating them in a sealed test cell, conveying the volatiles from the polymer sample by means of predried gas flowing at a known pressure and flow rate, transmitting the volatiles into a microwave transducer test cell, restraining the volatiles at a preset location in the beam of the microwave transducer test cell by restricting the outflow path of the volatiles to control resident time of the volatiles within the transmitted microwave energy, measuring the loss of microwave energy passing between an oscillator and detector in the transducer test cell when there is restrained water moisture near the open rectangular end of the oscillator antennae horn transverse to the elongated sides thereof, surrounding the transducer test cell with a microwave absorber to control the stray transmission of microwave energy between the oscillator and detector, and registering the output from the detector once most of the moisture has been obtained from the polymer sample as a measure of the loss of energy due to water moisture in the volatiles.

* * * * *